(12) United States Patent
Butler et al.

(10) Patent No.: US 8,444,697 B1
(45) Date of Patent: May 21, 2013

(54) SPINAL FUSION IMPLANT AND METHODS OF USE THEREOF

(75) Inventors: Daniel Butler, Summerville, SC (US); Donald Johnson, Isle of Palms, SC (US)

(73) Assignees: Daniel Butler, Summerville, SC (US); Donald Johnson, Isle of Palms, SC (US)

( * ) Notice: Subject to any disclaimer, the term of this patent is extended or adjusted under 35 U.S.C. 154(b) by 0 days.

(21) Appl. No.: 13/300,486

(22) Filed: Nov. 18, 2011

Related U.S. Application Data

(60) Provisional application No. 61/415,337, filed on Nov. 18, 2010.

(51) Int. Cl.
*A61F 2/44* (2006.01)

(52) U.S. Cl.
USPC .................................................. 623/17.16

(58) Field of Classification Search
USPC .......................................... 623/17.11–17.16
See application file for complete search history.

(56) References Cited

U.S. PATENT DOCUMENTS

| | | | | |
|---|---|---|---|---|
| 5,782,832 A | * | 7/1998 | Larsen et al. | 623/17.11 |
| 6,375,682 B1 | * | 4/2002 | Fleischmann et al. | 623/17.12 |
| 6,723,126 B1 | * | 4/2004 | Berry | 623/17.11 |
| 7,854,766 B2 | * | 12/2010 | Moskowitz et al. | 623/17.15 |
| 2004/0254644 A1 | * | 12/2004 | Taylor | 623/17.13 |
| 2005/0273174 A1 | * | 12/2005 | Gordon et al. | 623/17.16 |
| 2005/0278026 A1 | * | 12/2005 | Gordon et al. | 623/17.11 |

* cited by examiner

*Primary Examiner* — Kevin T Truong
*Assistant Examiner* — Michael Araj
(74) *Attorney, Agent, or Firm* — Buist, Byars & Taylor, LLC; Tiffany N. Butler

(57) ABSTRACT

The present invention comprises a method of stabilizing adjacent vertebral bodies with an expandable and size varying spinal fusion intervertebral implant device that comprises an expandable top(s) and, or bottom. The method comprises inserting the device into the intervertebral disc space. Once properly positioned, the method further comprises engaging the expandable body of the device by inserting and rotating a screw that runs along the longitudinal axis of the implant.

The expansion of the hinged top(s) and, or bottom may be used to restore normal balance, tilt and disc height of the vertebrae. Further, expansion of the device will engage surrounding vertebrae, thereby securely seating the device within the intervertebral disc space.

The method further comprises providing a bone material in or on the expandable cutting body of the device and, or in or on the intervertebral spacer portion of the device to permit fusion of the adjacent intervertebral bodies.

9 Claims, 25 Drawing Sheets

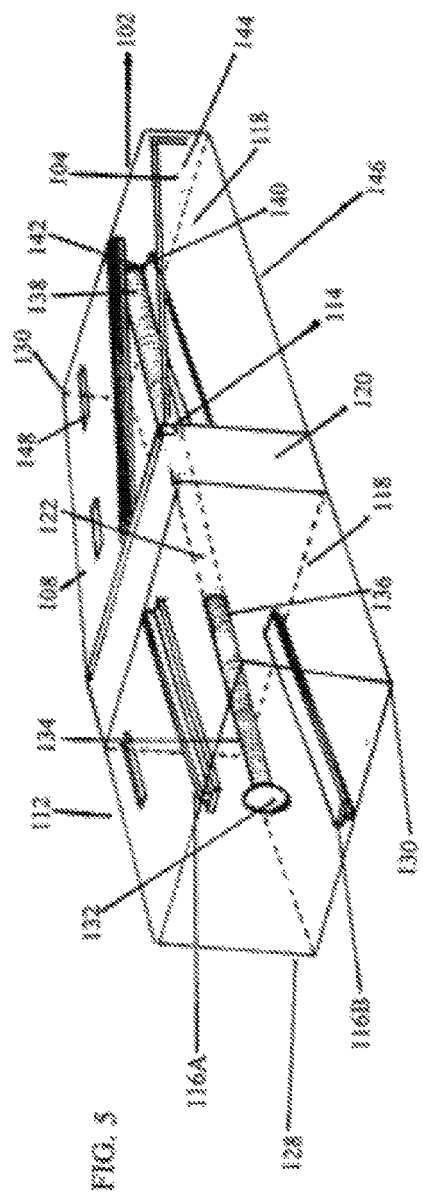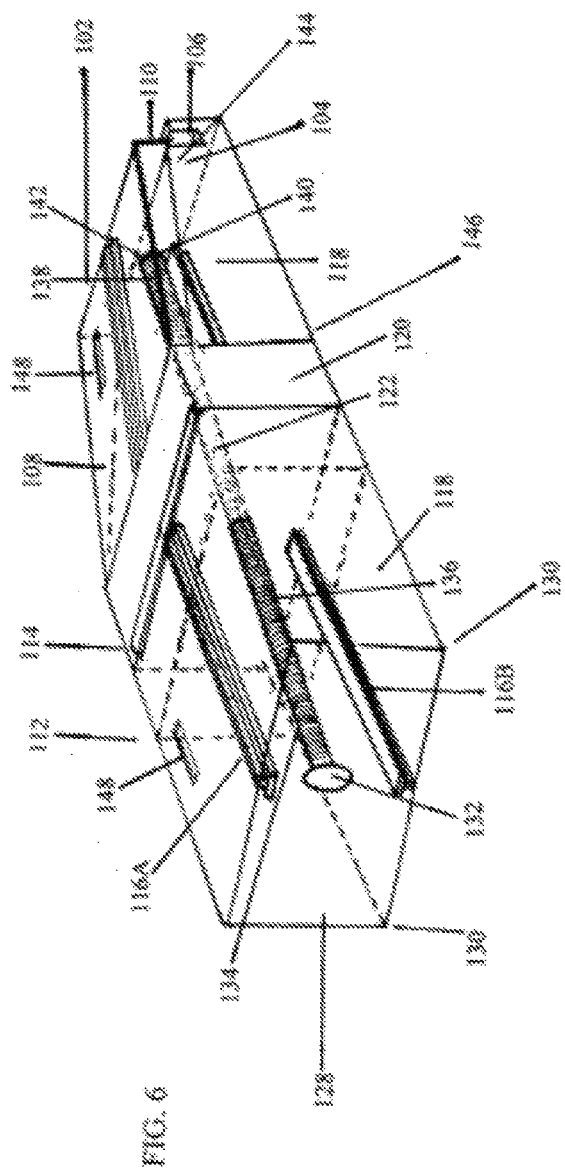

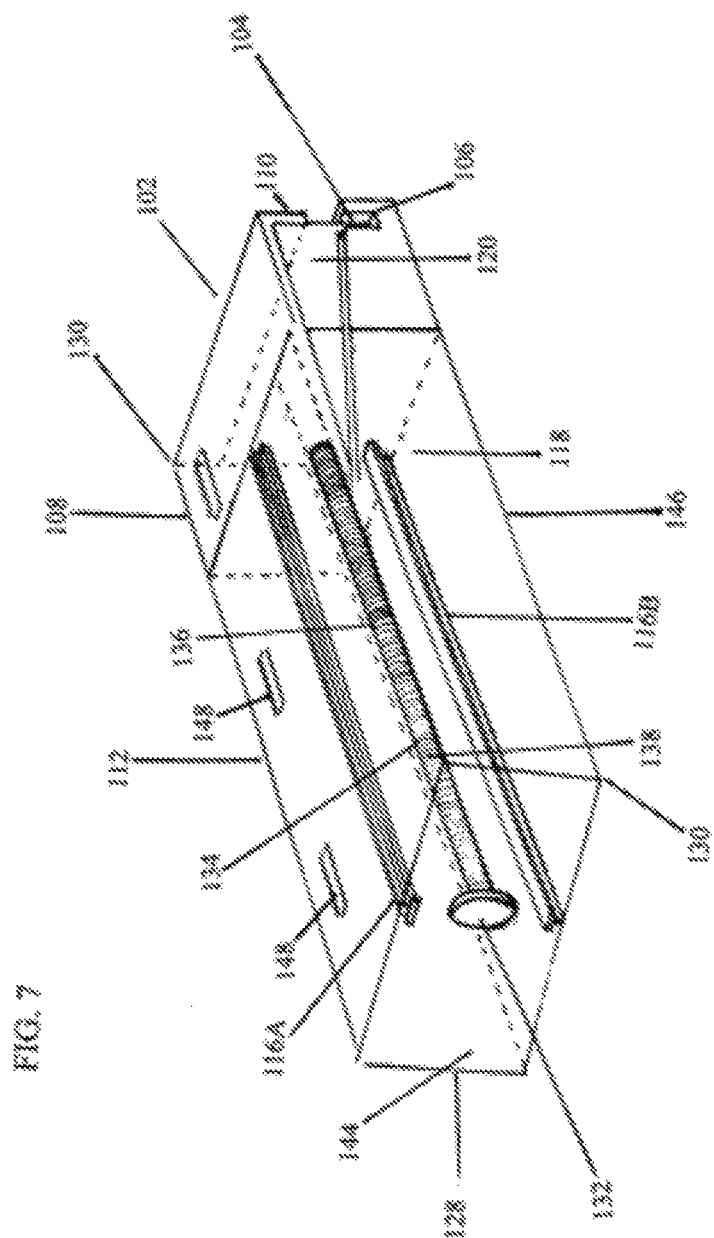

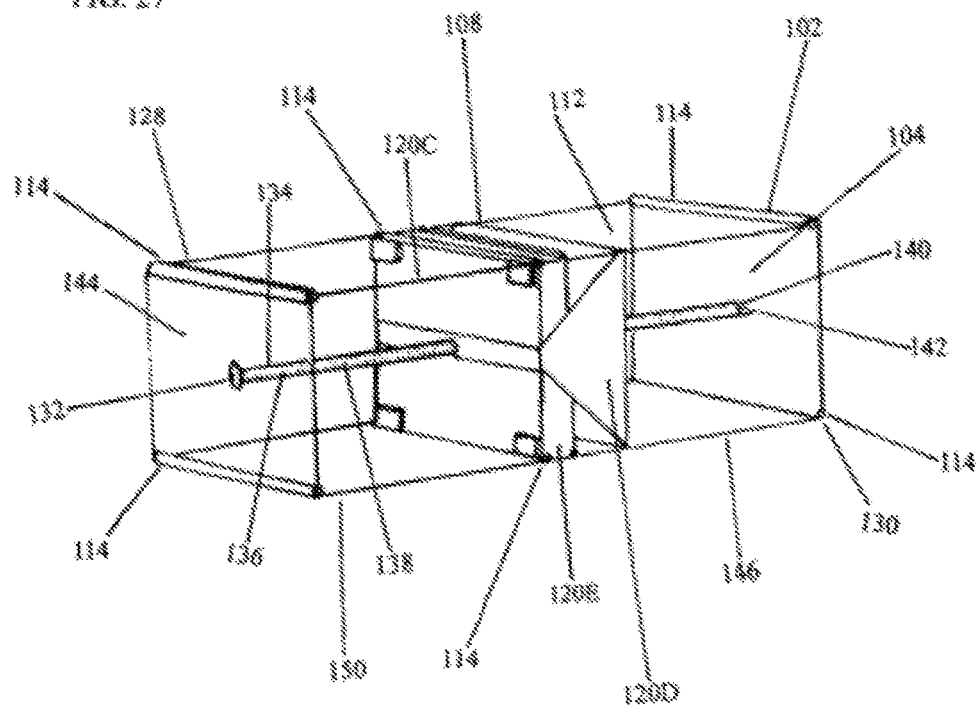

SPINAL FUSION IMPLANT AND METHODS OF USE THEREOF

CROSS REFERENCE TO RELATED APPLICATIONS

This application claims the benefit of the filing date of U.S. Provisional Application No. 61/415,337, which was filed on Nov. 18, 2010. The contents of U.S. application No. 61/415,337 are incorporated by reference as part of this application.

BACKGROUND

This application relates to spinal fusion implants and methods of use thereof.

The spine is a flexible structure that extends from the base of the skull to the tail bone. It contains 33 interconnected bones called vertebrae. Each vertebra is connected to the vertebra above and below at a facet joint. Each vertebra is separated from the vertebra above or below by a cushion-like, fibrocartilage called an intervertebral disc. There are 23 intervertebral discs in the human body: six in the cervical region (i.e. neck); 12 in the thoracic region (i.e. middle back); and five in the lumbar region (i.e. lower back). The human spinal column is configured so that the intervertebral discs act as shock absorbers for the spine. In addition, intervertebral discs act as a ligament that holds vertebrae together. Intervertebral discs also work with the facet joint to allow for slight movement of the spine; together, these structures allow the spine to bend, rotate and, or twist.

The spinal structure can become damaged as a result of degeneration, dysfunction, disease and, or trauma. More specifically, the spine may exhibit disc collapse, abnormal curvature, asymmetrical disc space collapse, abnormal alignment of the vertebrae and, or general deformity. Disc collapse, abnormal curvature, mis-alignment or deformity may lead to imbalance and tilt in the vertebrae. This may result in nerve compression, disability and overall instability and pain. Where a patient suffers from instabilities in the spine that cause pain and, or deformity, surgical intervention may be required.

Currently, surgical treatments to correct spinal deformities, like abnormal curvature and misalignment of the spinal column, involve manipulation of the spinal column by attaching a corrective device, such as rods, wires, hooks or screws, to straighten abnormal curvatures, appropriately align vertebrae of the spinal column and, or reduce further rotation of the spinal column. Interbody implants may be used to correct disc space collapse that results from conditions like Stenosis and Degenerative Disc Disease.

Spinal fusion is often necessary. A fusion is a surgical method wherein two or more vertebrae are joined together (fused) by way of interbody bone grafting to form a single bone. The current standard of care for interbody fusion requires surgical removal of all or a portion of the intervertebral disc. Removal of the intervertebral disc without replacement will likely cause the disc space to collapse; this may lead to further instability of the spine, nerve damage, abnormal joint mechanics and, or pain. Therefore, after removal of the intervertebral disc, a spinal implant is implanted in the interspace. In many cases, the fusion is augmented by a process called fixation. Fixation refers to the placement of screws, rods, plates, or cages to stabilize the vertebrae so that fusion can be achieved.

The traditional surgical course of treatment to correct abnormal curvatures, mis-alignment and, or general spinal deformities is invasive and often requires the dissection of muscle tissue. Such procedures lead to long recovery times, scarring, pain and excess blood loss.

More recently, a minimally invasive surgical fusion technique has been used to correct curvature and deformities of the spine. Under this minimally invasive technique, a lateral approach is taken to reach the spine through small incisions. Through these incisions, discs are removed and an intervertebral spine implant is placed in the intervertebral disc space to restore normal disc height. Fusion follows. A corrective device, such as rods, wires, hooks or screws, is used to stabilize the spine and promote fusion.

Minimally invasive spine surgery offers multiple advantages as compared to open surgery. Advantages include: minimal tissue damage, minimal blood loss, smaller incisions and scars, minimal post-operative discomfort, and relative quick recovery time and return to normal function.

SUMMARY

In an embodiment, a device of the present invention provides for an expandable interbody spacer. The interbody spacer comprises one or more moveable blocks secured by one or more rail systems and one or more screws. The interbody spacer further comprises one or more hinged tops capable of upward expansion. A hinged bottom capable of downward expansion is also contemplated. The interbody spacer is generally fabricated from a material that is rigid enough to withstand the compressive and torsional forces accepted by the intervertebral disc. Likewise, other component parts of a device of the present invention include any sterile, biocompatible material that is durable enough to withstand the compressive and torsional forces accepted by the intervertebral disc, such as a metal, a polymeric material or a ceramic.

In an embodiment, the present invention provides for a method of inserting a device of the present invention or any comparable device into the intervertebral disc space using an anterior (i.e. front), posterior (i.e. back) or lateral (i.e. side) approach to surgery. Once properly positioned, the method further comprises rotating the screw portion of a device of the present invention or that of a comparable device. Rotation of the screw engages a threaded channel that runs through the moveable block(s). This forces the moveable block(s) to the leading end of the implant and, or to the trailing end of the implant.

The mass of the moveable block(s) forces the hinged top(s) of the interbody spacer to expand upward. Similarly, the hinged bottom expand downwards. The upward expansion of the hinged top and, or downward expansion of the hinged bottom will force the adjacent vertebra to move. The expansion of the hinged top(s) and, or bottom may be used to restore normal balance, tilt and disc height of the vertebrae. Further, expansion of the device will engage surrounding vertebrae, thereby securely seating the device within the intervertebral disc space.

The method further comprises providing a bone material in or on the body of a device of the present invention and in the channels or cavities of the body of a device to permit fusion of the adjacent intervertebral bodies.

The methods of the present invention can be used to stabilize adjacent vertebral bodies in preparation of spinal fusion and restore proper balance, tilt, curvature and, or alignment of the vertebrae.

BRIEF DESCRIPTION OF THE DRAWINGS

The present invention will become more fully understood from the detailed description given herein and the accompanying drawings which are given by way of illustration only, and thus are not limiting of the scope of the present invention.

FIG. 5 is a perspective view of a device according to an embodiment of the present invention, in an unexpanded, non-deployed configuration.

FIG. 6 is a perspective view of a device according to an embodiment of the present invention, in a partially expanded, partially deployed configuration.

FIG. 7 is a perspective view of a device according to an embodiment of the present invention, in an expanded, deployed configuration.

FIG. 27 is a perspective view of a device according to an embodiment of the present invention, in an unexpanded, non-deployed configuration.

BRIEF DESCRIPTION OF THE DRAWINGS

Reference Numerals

| Part | Reference Number |
| --- | --- |
| Vertebral body | V |
| Disc space | D |
| Implant | 100 |
| Leading end | 102 |
| Interior wall of leading end | 104 |
| Groove (to accommodate expandable top) | 106 |
| Expandable top | 108 |
| Lip (on expandable top) | 110 |
| Top | 112 |
| Hinge | 114 |
| Top Guide Rail | 116A |
| Bottom Guide Rail | 116B |
| Cavity | 118 |
| Moveable Block | 120 |
|  | 120A |
|  | 120B |
|  | 120C |
|  | 120D |
|  | 120E |
| Threaded channel (through moveable block) | 122 |
| Unthreaded channel (through moveable block) | 124 |
| Channel for top railing | 126A |
| Channel for bottom railing | 126B |
| Trailing end | 128 |
| Corner | 130 |
| Screw head | 132 |
| Screw | 134 |
| Screw Shaft | 136 |

-continued

| Part | Reference Number |
|---|---|
| Helical Flighting | 138 |
| Distal End of Screw | 140 |
| Mounted Rotator | 142 |
| Interior wall of trailing end | 144 |
| Bottom | 146 |
| Graft Window | 148 |
| Expandable Bottom | 150 |
| Stopper | 152 |

DETAILED DESCRIPTION

The embodiments disclosed herein are discussed in the context of an interbody implant and spinal fusion because of the applicability and usefulness in such a field. More specifically, the interbody implant and methods of use thereof may be use to correct general spinal deformities, such as disc collapse, abnormal curvature of the spine (scoliosis) and misalignment of the vertebrae (spondylolidthesis).

As such, various embodiments of the present invention can be used to properly space adjacent vertebrae, recreate proper disc height, provide proper support in preparation for spinal fusion, and restore proper balance, tilt, curvature and, or alignment of the vertebrae of the spinal column.

First Embodiment

FIGS. 1, 2, 3, 4, 5, 6, 7 and 8

Figure 1:
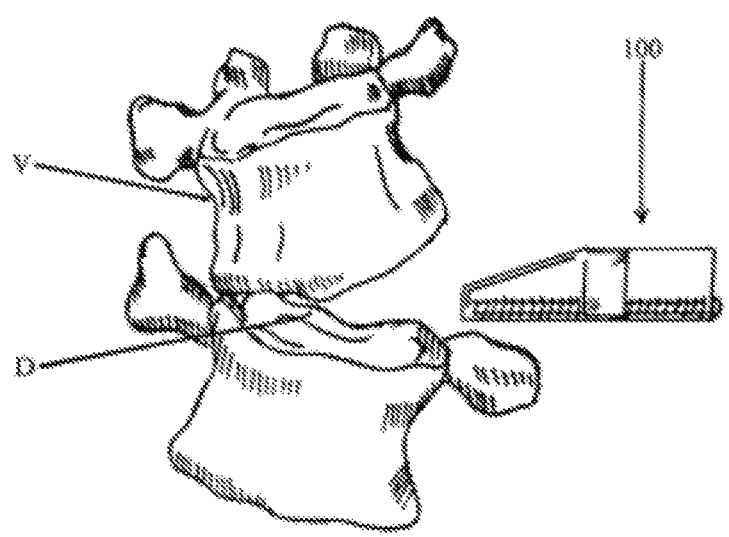
FIG. 1 is a schematic illustration of a device of the present invention prior to insertion in the intervertebral disc space in an unexpanded, non-deployed configuration.
Figure 2:
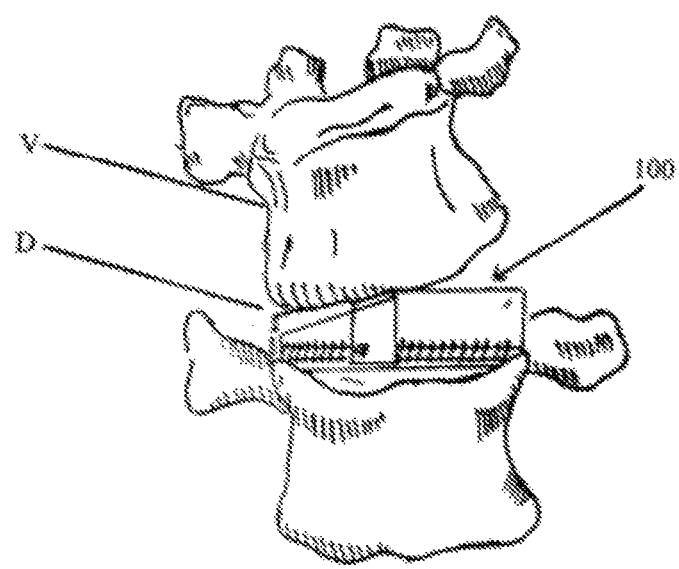
FIG. 2 is a schematic illustration of a device of the present invention positioned in the intervertebral disc space in a partially expanded, partially deployed configuration.
Figure 3:
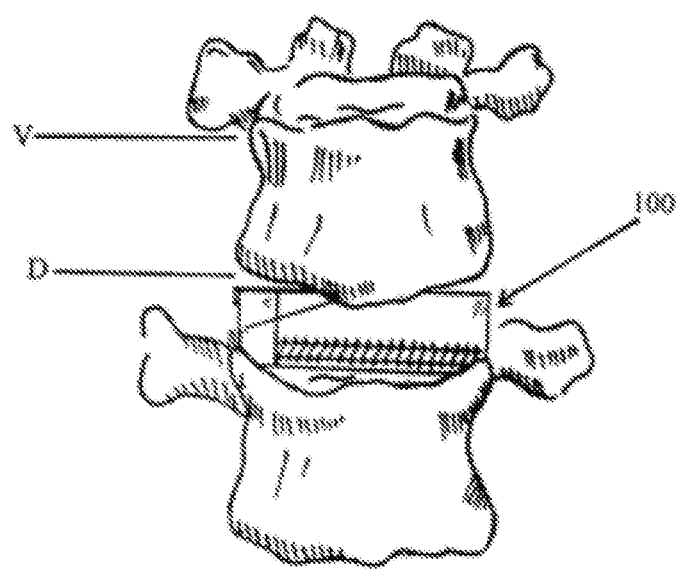
FIG. 3 is a schematic illustration of a device of the present invention positioned in the intervertebral disc space in an expanded, deployed configuration.

FIG. 1 (schematic view in non-deployed, unexpanded state), FIG. 2 (schematic view in partially deployed, partially expanded state), and FIG. 3 (schematic view in deployed, expanded state), generally depicts an expandable interbody spacer, interbody fusion implant or intervertebral implant 100. The implant 100 is designed for implantation across a disc space D between two adjacent vertebral bodies V.

The implant 100 is sized to fit the anatomy of the patient by way of sizing trials. The device is designed to fit into the cavity of the intervertebral disc space D. In most embodiments, the device will generally range from about 0.5 to 35 millimeters (mm) in width. The device will generally range from 1 to 100 millimeters (mm) in length.

In an embodiment, the implant comprises the shape of a rectangular prism, wherein the leading end 102 of the implant transitions from a wedge-like shape in its non-deployed, unexpanded state (FIG. 1) to a rectangular shape in its partially expanded and expanded state (FIG. 2 and FIG. 3).

However, in an alternate embodiment, the overall shape of the implant may be of any shape that can be inserted into the intervertebral disc space. For example, it is contemplated that the implant may have a cylindrical, bullet, cuboidal or polygonal shape. Similarly, the leading end of the implant may comprise any shape that allows for insertion of the implant into the intervertebral disc space. Non-limiting examples include a rounded, beveled, rectangular, or polygonal leading end.

In one aspect, the outer corners of the implant are beveled or rounded so that it can be implanted in and fit into the intervertebral disc space without snagging. In other embodiments, the corners of the intervertebral disc spacer can be of any shape that will fit into the intervertebral disc space.

Figure 4:
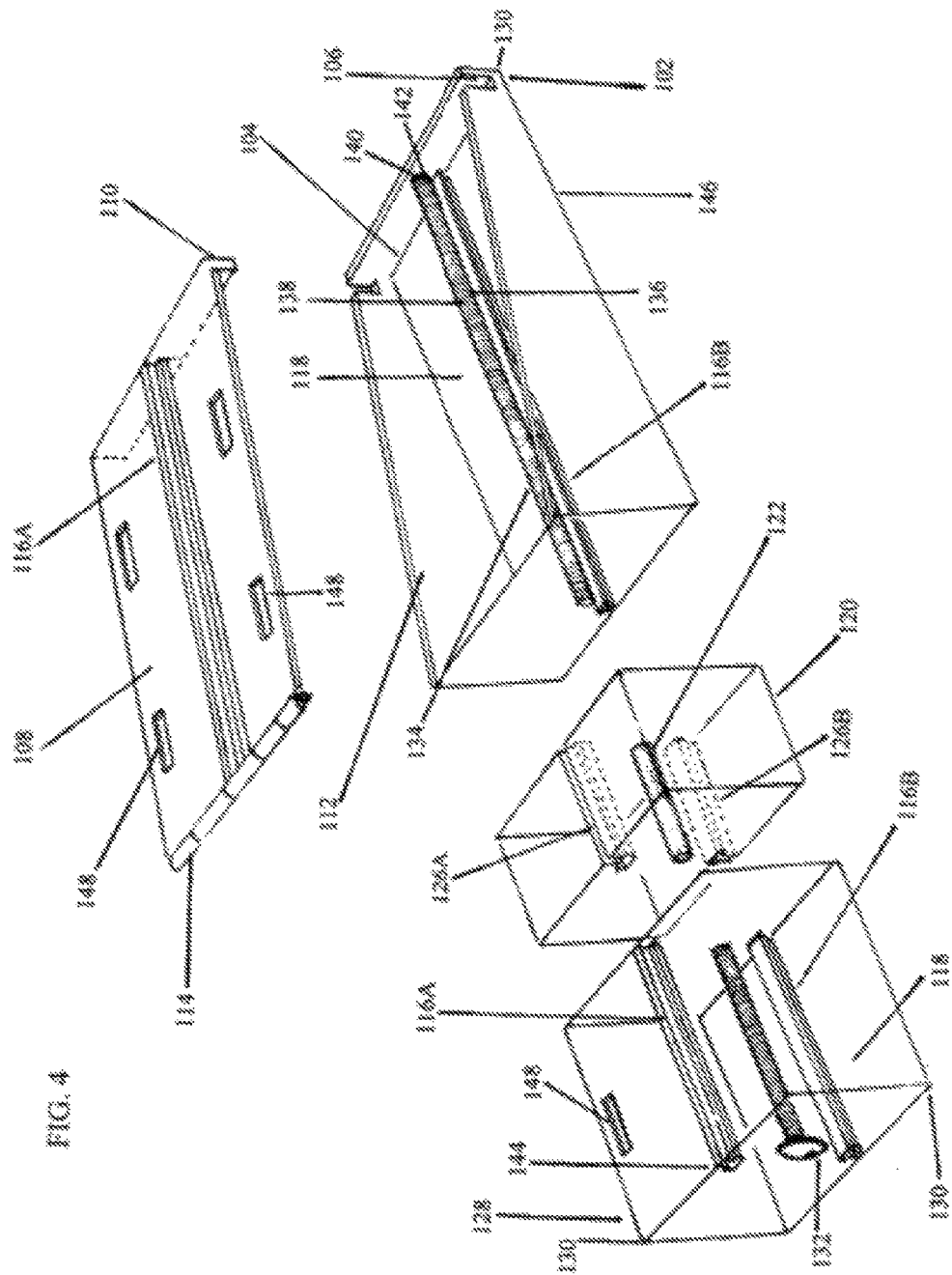
FIG. 4 is an exploded view of a device according to an embodiment of the present invention.

Referring to FIG. 4, the implant comprises: (i) a leading end 102; (ii) an expandable top 108; (iii) secured to the interbody spacer by a hinge 114; (iv) a moveable block 120; (v) secured by a rail 116A, 116B; and (v) the shaft of a screw 136; (vi) followed by the trailing end 128 of the interbody implant. As will be more fully explained herein, the above parts work in tandem to facilitate the expansion of the implant.

The leading end 102 of the implant comprises a wedge-like leading end 102 in its non-deployed, unexpanded state (see also FIG. 1). However, the leading end 102 transitions to a more rectangular shape as the expandable top 108 expands (see also FIGS. 2 and 3). The wedge-like shape of the leading end 102 is formed wherein the expandable top 108 of the implant connects to the hinge 114 located on the top 112 of the device and slants downward to form an acute angle.

However, it is contemplated that the leading end of the device in a non-deployed, unexpanded state may comprise any shape other than a wedge-shape that allows for insertion of the implant into the intervertebral disc space. For example, it is contemplated that in an alternate embodiment, the leading end of a device of the present invention may comprise a rounded, beveled, rectangular, or polygonal tip at its distal end. In addition, in an alternate embodiment, the angling of the expandable top 108 may vary.

The leading end 102 of the implant comprises a groove or notch 106 designed to complement and accommodate the lip 110 on the expandable top 108. A groove 106 is located on the right and left side of the leading end 102. In alternate embodiments, it is contemplated that a groove will not be present on the leading end of the device.

The top 112 of the implant is divided latitudinally by a hinge 114. A portion of the top 112 comprises and expandable top 108. The expandable top 108 is located on the leading end 102 of the implant. It is secured by a hinge 114 that runs along the latitudinal axis (not shown) of the implant. In this embodiment, the expandable top 108 is deployed and expanded by way of applied force created by the rotational movement of a screw 134.

The expandable top 108 of the implant contains a lip 110 that is designed to complement and accommodate the groove 106 located on the leading end 102 of the implant. In alternate embodiments, it is contemplated that a lip structure will not be present on the expandable top of the implant.

The implant comprises a plurality of bone graft windows 148 located on the top 112 of the implant and on the bottom 146 of the implant. Each graft window 148 extends from the inner surface of the implant to the outer surface of the implant. Each graft window 148 comprises an overall rectangular shape. In the present embodiment, the graft windows 148 on the top 112 of the implant are symmetrical to the graft windows 148 on the bottom 146 of the implant.

In this embodiment, the graft windows 148 are organized such that there are two rows of graft windows 148 on the top 112 of the implant and two rows of graft windows 148 on the bottom 146 of the implant. Each row comprises three graft windows 148. There is a row of graft windows 148 located on the left side of the implant and a row of graft windows 148 located on the right side of the implant. Each row extends longitudinally from the leading end 102 of the implant to the trailing end 128 of the implant. Each row of graft windows runs parallel to the other. In addition, in the present embodiment, the graft windows 148 are evenly spaced in relation to one another.

In the present embodiment, the graft windows 148 on the implant allow for receipt of bone material into a cavity 118. Additionally, the graft windows 148 of the implant provide a pathway by which bone ingrowth can be achieved when either the graft windows 148 or the cavity 118 is filled with a substance that encourages bone growth. As such, the graft windows 148 are sized so that they are in proportion with the intervertebral spacer and are large enough to permit bone ingrowth, yet small enough not to compromise the overall structure of the implant. However, in most embodiments, the graft windows 148 generally range from 0.1 to 5 millimeters (mm) in width and from 0.1 to 25 millimeters (mm) in length.

In an alternate embodiment, it is contemplated that there may be more or less than six graft windows on either the top or bottom portion of the implant. Further, in an alternate embodiment, it is contemplated that there may be a single long graft window that runs the length of the implant, or a series of long graft windows that run the length of the implant. In addition, the graft windows may comprise any shape, structure or proportion in accordance with their intended functions.

The trailing end 128 of the implant comprises a screw head 132. The screw head 132 can be configured to accept the distal end of a driving tool (not shown) to assist with the placement of the implant into the intervertebral disc space. In addition, the driving tool (not shown) is used to rotationally turn screw head 132 and deploy the moveable block 120.

In an alternative embodiment, the implant may also comprise a locking nut (not shown) to threadably engage shaft 136 of the screw 134. The locking nut can also be configured to accept the distal end of a driving tool to tighten the nut onto shaft 136. The locking nut can have a hexagonally shaped outer surface to engage a driver tool having a distal end having a complementary shaped inner surface.

Although, in the above described embodiments, the driving tools used to rotate the screw and nut are separate devices, a single device can be used to rotate each component. Further, although in the above described embodiments, the devices used to rotate the screw and nut are independently actuatable since one component is held stationary while the other component is urged distally or proximately to expand the expandable top of the device. In other situations, it may be necessary to rotate both screw and nut simultaneously to deploy the expandable top of the implant. In such an embodiment, the installation tools used to rotate the screw may be a single device that rotates the components in concert.

The implant comprises a hollow interior 118 that is in constant communication with the interior walls of the implant. The hollow interior comprises: (1) a moveable block 120 that is secured by; (2) the shaft 136 of a screw 134; (3) a top rail 116A; and (4) a bottom rail 116B.

The moveable block 120 comprises an overall rectangular prism shape. It is sized to fit within the cavity 118 of the implant. In most embodiments, the moveable block 120 will generally range from about 0.5 to 25 millimeters (mm) in width. The device will generally range from 0.5 to 25 millimeters (mm) in length. In an embodiment, the moveable block 120 is flush with the interior walls of the implant.

However, in alternate embodiments, it is contemplated that the size of the moveable block and proximity of the moveable block may vary so long as the moveable block operates in accordance with its intended function. In addition, in an alternate embodiment the overall shape of the moveable block may vary. Non-limiting examples of the overall shape of the moveable block include a bullet-like shape, a cylindrical shape, a cuboidal shape, a polygonal shape or a wedge-like shape.

Figure 8:
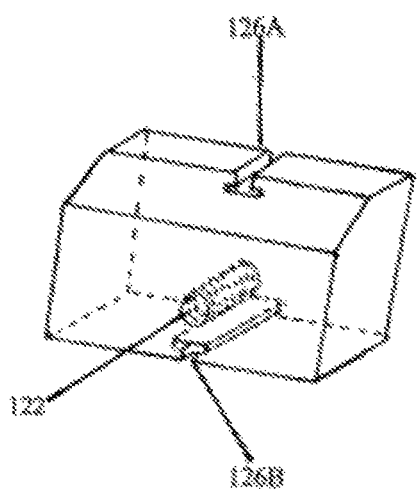
FIG. 8 is a perspective view of the moveable block of a device according to an embodiment of the present invention and as depicted in FIGS. 5, 6 and 7.

Further, as depicted by FIG. 8, in an alternate embodiment, the top of the moveable block may be angled to form a wedge-like tip. It is contemplated that in certain embodiments, this structure may aid in the overall movement of the moveable block with the body of the implant. In addition, this structure may aid in the expansion of the expandable top.

In its non-deployed position, the moveable block 120 is centered on the latitudinal axis (not shown) of the implant (see also FIGS. 1 and 5). As the implant is deployed, the moveable block 120 travels from the center of the implant to the leading end 102 of the implant (see also FIGS. 2 and 6 (partially deployed, partially expanded) and 3 and 7 (deployed and expanded)). In alternate embodiments, it is contemplated that the moveable block may be positioned at any position that is reasonably calculated to work in accordance with its intended function.

Referring to FIGS. 4 and 8, the moveable block 120 comprises three channels: (1) a threaded channel 122 designed to accommodate the screw shaft 136; (2) a channel designed to accept the top railing 116A of the implant; and (3) a channel designed to accept the bottom railing 116B of the implant.

The moveable block 120 comprises a threaded channel 122 designed to accept the shaft 136 of a screw. The threaded channel 122 is generally cylindrical in shape. The threaded channel 122 is sized to accommodate the anatomy of the screw shaft 136. Likewise, the threading is designed to engage the flighting 138 of the screw shaft 136.

Referring to FIG. 4, the screw shaft 136 runs along the longitudinal axis (not shown), from the interior wall of the leading end 104 of the device to the interior wall of the trailing end 144 of the implant. In an embodiment, a screw 134 is sized to accommodate the body of the implant, and the work area of the surgeon. However, generally the screw 134 will range from about 1 millimeter to 30 millimeters (mm) in diameter. The screw 136 generally ranges from 1 to 100 millimeters (mm) in length.

In this embodiment, the distal end 140 of the screw 134 is not tapered. However, in other embodiments, it is contemplated that the distal end of the screw may taper.

The shaft 136 comprises a plurality of helical radial blades known in the art as flighting 140. The flighting 138 forms a spiral like shape around the diameter of the shaft 136. The flighting 138 extends the length of the shaft. It is contemplated that the flighting will stop at any distance that is reasonably calculated to allow the shaft of the securely to connect to the interior wall of the implant. This will generally range between 0.1 millimeter (mm) and 20 millimeters (mm) from the tip of the shaft.

In an alternate embodiment, the shaft of the screw may compromise any number of helical blades or a plurality of helical blades to form the flighting of the screw shaft. It is also contemplated that the blades the may be of any shape shape or proportion that is in accordance with their intended function.

The shaft 138 of the screw is fixed in place at the distal end 140 of the screw 134 by a mounted rotator 142. The mounted rotator fixes the distal end 140 of the screw 134 in place while allowing the body of the screw 134 to freely rotate. The screw head 132 is located at the proximal end of the screw 134. The screw 134 is affixed in such a manner so as to permit the rotation of the screw head 132 by applied force.

Referring to FIGS. 4 and 8, the moveable block 120 comprises two channels designed to accept guide rails 116A, 116B. In the present embodiment, the top guide rail 116A is located towards the top 112 of the implant. Similarly, the bottom guide rail 116B located towards the bottom 146 center of the implant.

Referring to FIG. 4, the guide rails 116A, 116B run along the longitudinal axis (not shown) of the implant. The guide rails 116A, 116B extend from the interior wall of the leading end 104 of the implant to the interior wall of the trailing end 144 of the implant.

FIG. 5 depicts the implant in a non-deployed, unexpanded state. In an non-deployed, unexpanded state, the leading end 102 of the implant comprises a wedge-like shape. The moveable block 120 is centered on the latitudinal axis (not shown) of the implant.

FIG. 6 depicts the implant in a partially deployed, partially expanded state. As will be more fully explained herein, the expandable top 112 of the leading end 102 of the implant is designed to expand upwards. With the expansion of the expandable top 112, the overall shape of the implant will transition to a more rectangular leading end as compared to the implant in a non-deployed, unexpanded state (see FIGS. 1 and 5 for comparison). The moveable block 120 in a partially deployed, partially expanded state is located between the center latitudinal axis the implant and the leading end of the implant.

FIG. 7 depicts the implant in a deployed and expanded state. As will be more fully explained herein, the expandable top 112 of the leading end 102 of the implant is designed to expand upwards. With the expansion of the expandable top 112, the overall shape of the implant will transition to a rectangular leading end as compared to the implant in a non-deployed, unexpanded state (see FIGS. 1 and 5 for comparison). The moveable block 120 in a deployed, partially expanded state is located at or near the leading end 102 of the implant.

The components of a device of the present invention can be fabricated from various materials to allow such components to operate according to their intended function. For example, the components of the body of the implant can be fabricated from any sterile, biocompatible material that is flexible enough such that it can be compressed when axial forces are applied thereto, yet be strong enough to be able to withstand compressive and torsional forces for a long enough period of time so as to permit fusion. For example, it can be fabricated from a deformable material such as a flexible metal or elastomeric polymer. Non-limiting examples of suitable materials include titanium, expandable polytetraflourethylene (ePTFE), or polytheretherketone (PEEK).

The screw, locking nut (if used) and hinge components of a device of the present invention can be fabricated from any sterile, biocompatible material that is durable enough to withstand the compressive and torsional forces of the surrounding adjacent vertebrae. Suitable materials include metal, polymeric material or ceramic material.

Non-limiting examples of a metal include stainless steel, cobalt-chrome or titanium alloys. Non-limiting examples of plastics include a blend of polycaprolactone and polyglycolide, a blend of polyactide and polyglycolide, pure polydioxanone, poly (ethylene oxide), poly (butylene terephthalate), polyorthoester, or polyhydroxybutyrate. In certain embodiments, the components of the device are fabricated from biodegradable materials such as polycaprolactone, poly (L-lactide), polyglycol, poly(D,L-lactide), poly(D,L-lactide-co-glycol), poly(D,L-lactide-cocaptrolactone), polydioxanone, copolyoxalates and polycarbonates, such as, for example, polyglycol-co-trimethylenecarbonate and poly (glutamine-co-leucine).

The bone material used in the above described embodiments can be a bone graft material or a BMP. Bone graft materials are well known in the art and include both natural and synthetic materials. For example, the bone graft material can be an autologous or autograft, allograft, xenograft, or synthetic bone graft. BMPs are also well known in the art and include BMP-2, BMP-3, BMP-4, BMP-5, BMP-6 (VGR-1), BMP-7 (OP-1), BMP-8, BMP-9, BMP-10, BMP-11, BMP-12, BMP-13, BMP-14 and BMP-15. The bone material can also include other therapeutic agents such as anti-microbial agents or antibiotics.

Operation

FIGS. 1, 2, 3, 4, 5, 6, and 7

The manner of using a device of the present invention is similar to that for interbody spinal implants currently known in the art. First, the damaged, displaced or unhealthy intervertebral disc is surgically removed. After removal of the damaged, displaced or unhealthy disc, an interbody spinal implant, like the device of the present invention, an improved spinal implant, is implanted in the same interspace.

Referring to FIGS. 1 and 2, the device 100 is securely seated within the intervertebral disc space D between adjacent vertebrae V. Referring to FIGS. 1 and 5, the wedge-shaped leading end 102 of the implant is first inserted so that the leading end 102 of the implant is the end of the device that is closest to the inner portion of the spinal column. FIG. 2 depicts the device 100 in a partially deployed, partially expanded state while positioned generally between adjacent vertebrae V of the spine. Thus, the device 100 can be used to provide the proper spacing between adjacent pending the healing of a fusion. FIG. 6 provides a perspective view of the implant in a partially deployed, partially expanded configuration.

Referring to FIGS. 5 and 6, the method further comprises providing a bone material in or on the implant to permit fusion of the adjacent intervertebral bodies. Bone graft windows 148 and cavity 118 also allow for receipt of bone material.

Referring to FIGS. 2 and 6, once properly positioned, the method further comprises engaging the screw head 132 of the implant. The driving tool (not shown) is used to rotationally turn screw head 132 and locking nut (if used).

Although, in the above described embodiments, the driving tools used to rotate the screw and nut are separate devices, a single device can be used to rotate each component. Further, although in the above described embodiments, the devices used to rotate the screw and nut are independently actuatable since one component is held stationary while the other component is urged distally or proximately to expand the expandable body of the device. In other situations it may be necessary to rotate both screw and nut simultaneously to deploy the expandable cutting body of the device. In such an embodiment, the installation tools used to rotate the screw may be a single device that rotates the components in concert.

The screw head 132 is rotated in such a manner that the rotation of the screw shaft 136 forces the flighting 138 of the screw 134 to engage the threaded channel 122 that runs through the moveable block 120.

The moveable block 120 is thereby forced toward the leading end 102 of the device. The guide rails 116A, 116B of the implant secure the moveable block 120 within the cavity 118 and further ensure that the moveable block 120 follows the desired path.

As the moveable block 120 travels towards the leading end 102 of the implant, the mass of the moveable block 120 forces the expandable top 108 to expand upwards. The hinge 114 secures the expandable top 108 in place while permitting it to expand upward. The mass of the moveable block 120 combined with the upward expansion of the expandable top 108 forces the adjacent vertebra to move. This expansion may be used to restore normal balance, tilt and disc height of the vertebrae. Further, expansion of the device will engage surrounding vertebrae, thereby securely seating the device within the intervertebral disc space.

FIGS. 3 and 7 depict the implant in a fully deployed, fully expanded state. Referring to FIGS. 3 and 7, the screw may be engaged as needed to obtain the desired degree of expansion.

Alternate Embodiments

FIGS. 9, 10, 11, 12, 13, 14, 15, 16, 18, 19, 20, 21, 22, 23, 24, 25, 26A, 26B, 26C, 27 and 28

There are various possibilities with regard to the structure of a device of the present invention, specifically the expandable top portion of the implant may be altered.

Referring to FIGS. 9, 10, 11, 12, 13, 14, 15, 16 and 17, in other embodiments, it is contemplated that the device will comprise an expandable top 108 on the leading end 102 of the device and an expandable top 108 on the trailing end 128 of the device.

Figure 9:
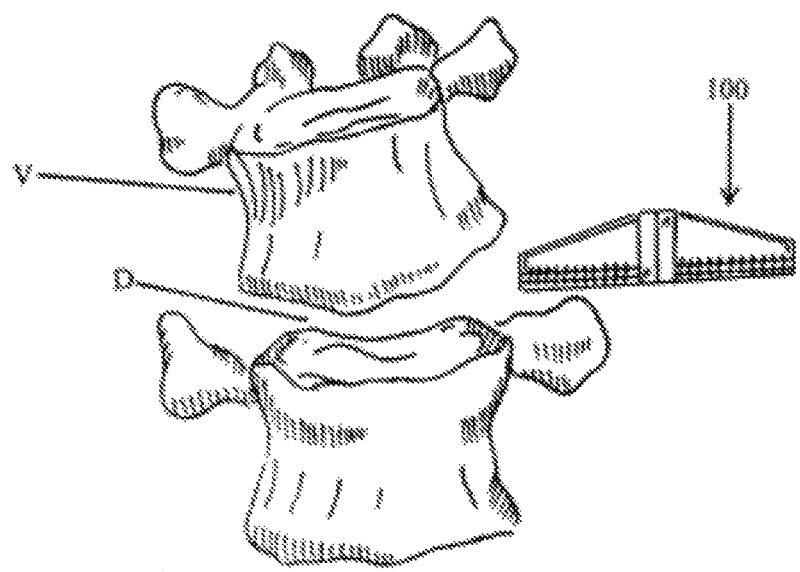
FIG. 9 is a schematic illustration of a device of the present invention prior to insertion in the intervertebral disc space in an unexpanded, non-deployed configuration.
Figure 10:
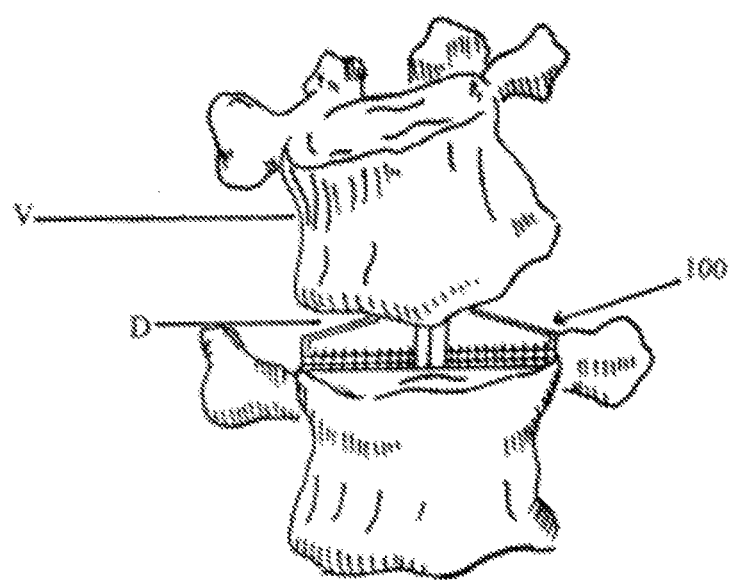
FIG. 10 is a schematic illustration of a device of the present invention positioned in the intervertebral disc space in an unexpanded, non-deployed configuration.
Figure 11:
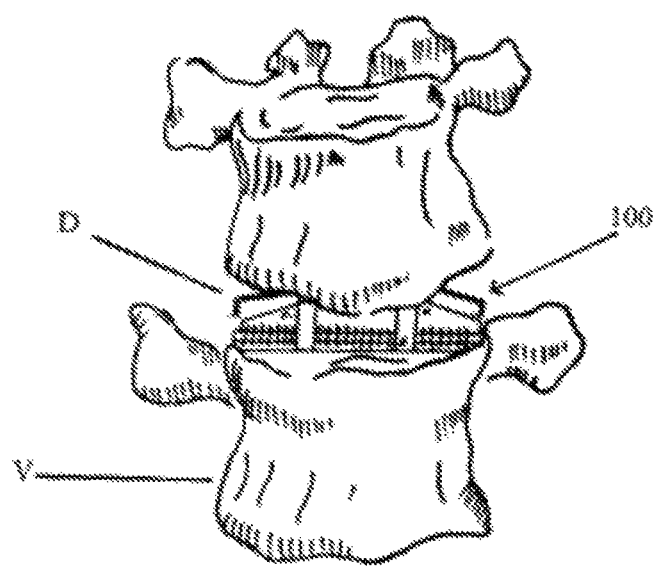
FIG. 11 is a schematic illustration of a device of the present invention positioned in the intervertebral disc space in a partially expanded, partially deployed configuration.
Figure 12:
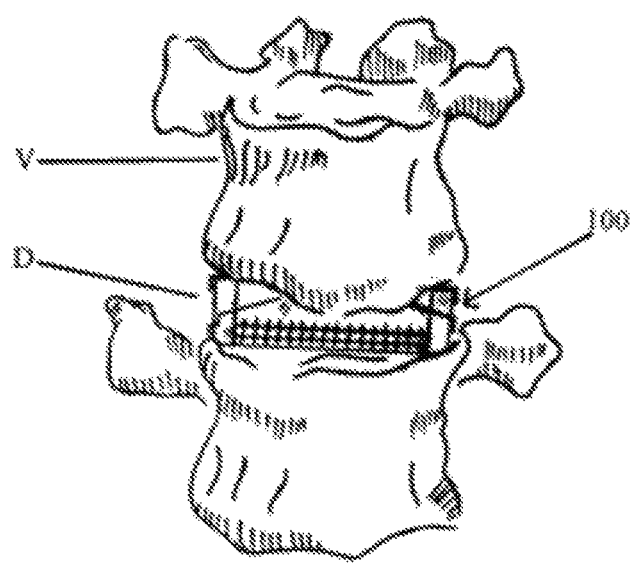
FIG. 12 is a schematic illustration of a device of the present invention positioned in the intervertebral disc space in an expanded, deployed configuration.

FIG. 9 (schematic view in non-deployed, unexpanded state), FIG. 10 (schematic view in non-deployed, unexpanded state), FIG. 11 (schematic view in partially deployed, partially expanded state), and FIG. 12 (schematic view in deployed, expanded state), generally depict an intervertebral implant 100. The implant 100 is designed for implantation across a disc space D between two adjacent vertebral bodies V.

Figure 14:
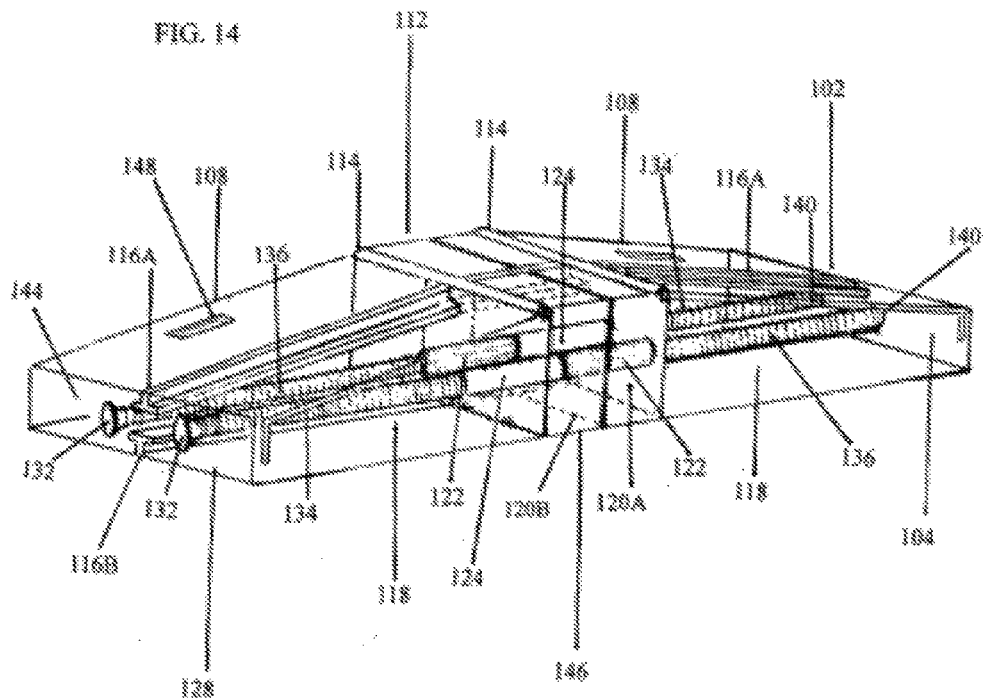
FIG. 14 is a perspective view of a device according to an embodiment of the present invention, in an unexpanded, non-deployed configuration.
Figure 15:
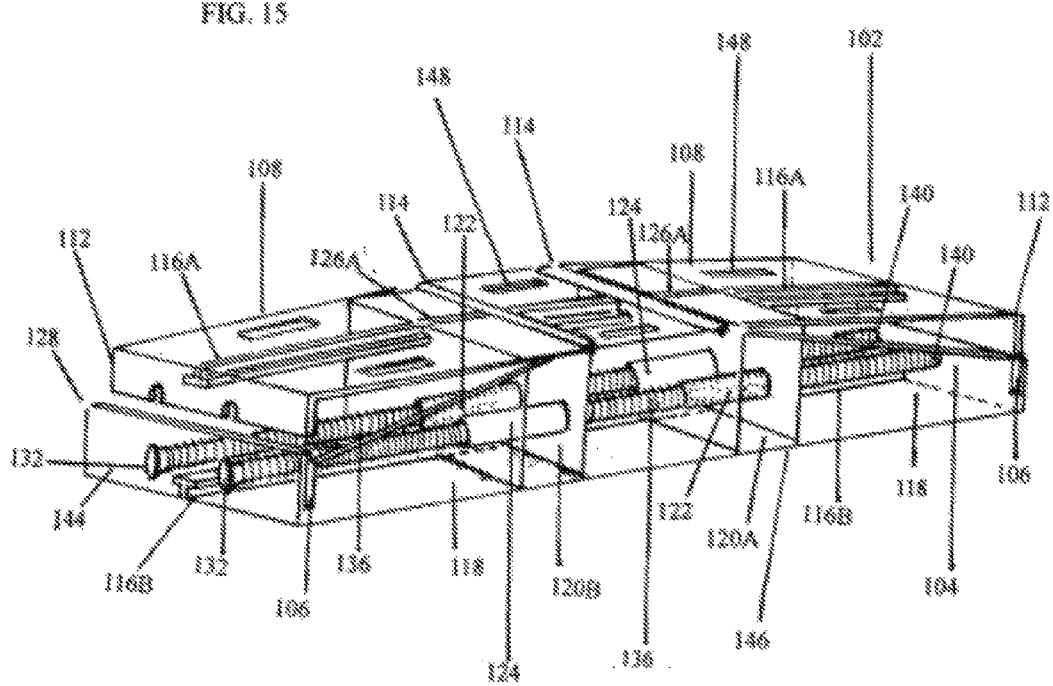
FIG. 15 is a perspective view of a device according to an embodiment of the present invention, in a partially expanded, partially deployed configuration.
Figure 16:
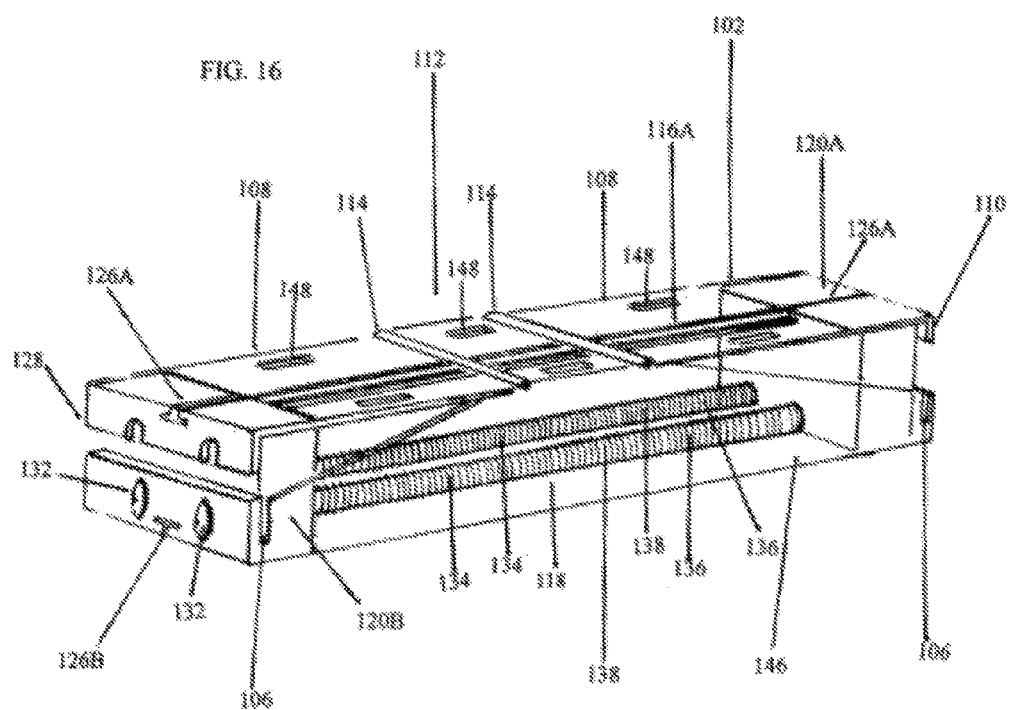
FIG. 16 is a perspective view of a device according to an embodiment of the present invention, in an expanded, deployed configuration.

Referring to FIGS. 14, 15 and 16, In this embodiment, the implant comprises a leading end 102 with an expandable top 108 that is secured to the body of the implant with a hinge 114. Likewise, the implant comprises a trailing end 128 with an expandable top 108. The interior of the implant contains two moveable blocks 120A, 120B. The moveable blocks 120A, 120B are secured in place by a top rail 116A, bottom rail 116B and screw 134. As will be more fully explained herein, the above parts work in tandem to facilitate the expansion of the implant.

Both the leading end 102 and the trailing end 128 of the implant comprise a wedge-like shape in its non-deployed, unexpanded state (see also FIGS. 9 and 10). However, the leading end 102 and trailing end 128 transition to a more rectangular shape as the expandable top 108 expands (see also FIGS. 14 and 15). The wedge-like shape of the leading end 102 and trailing end 128 are formed where the expandable top 108 of the device connects to the hinge 114 located on the top 112 of the device and slants downward to form an acute angle.

The implant comprises two screws 134. Each screw runs along the longitudinal axis (not shown) of the implant. The trailing end 128 of the implant comprises two screw heads 132. Each screw head 132 can be configured to accept the distal end of a driving tool (not shown) to assist with the placement of the implant into the intervertebral disc space and, or to rotationally turn screw head 132.

The shaft 136 of the screw 134 extends from the interior wall of the trailing end 144 to the interior wall of the leading end 104 of the implant. As in the first embodiment, the shaft 136 contains a plurality if helical blades known in the art as flighting 138. In this embodiment, the direction of the flighting 138 of each screw 134 is opposite from the other.

The implant comprises a cavity 118 that is in constant communication with the interior walls of the implant. The hollow interior comprises: (1) two moveable blocks 120A, 120B that are secured by; (2) two screw shafts 136; (3) a top guide rail 116A; and (4) a bottom guide rail 116B.

Each moveable block 120A, 120B comprises an overall rectangular prism shape. However, referring to FIG. 17, it is contemplated that the top of the moveable block may be angled so as to provide a wedge-like tip.

Each moveable block 120A, 120B is sized to fit within the cavity 118 of the implant. In this embodiment, the moveable blocks 120A, 120B will generally range from about 0.25 to 15 millimeters (mm) in width. The device will generally range from 0.5 to 25 millimeters (mm) in length. In an embodiment, the moveable block 120A, 120B is flush with one another and the interior walls of the implant.

In its non-deployed position, the moveable blocks 120A, 120B are centered on the latitudinal axis (not shown) of the implant (see also FIGS. 9, 10, and 14). As the implant is deployed, the moveable blocks 120A, 120B travel from the center of the implant. Moveable block 120A is nearest to the leading end 102 of the implant. When deployed, moveable block 120A travels to the leading end 102 of the implant. Moveable block 120B is nearest to the trailing end 128 of the implant. When deployed, moveable block 120B travels to the trailing end 128 of the implant (see also FIGS. 11 and 15 (partially deployed, partially expanded) and FIGS. 12 and 16 (deployed and expanded)).

Figure 13:
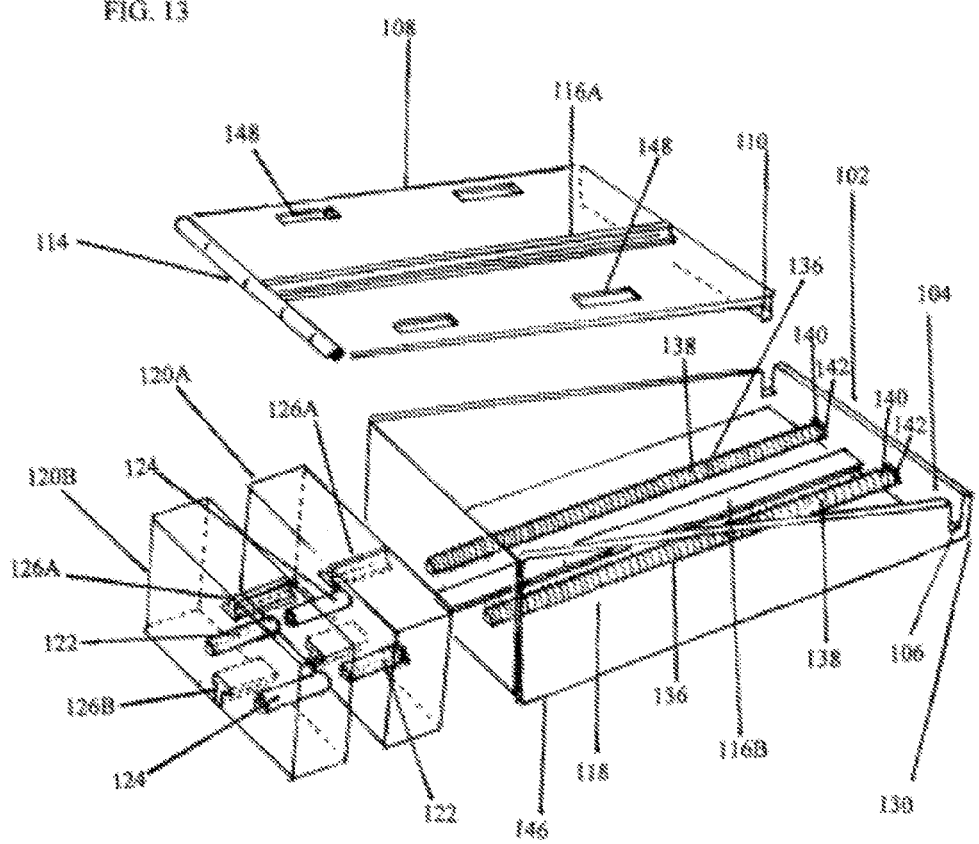
FIG. 13 is an exploded view of the leading end, expandable top and moveable blocks of a device according to an embodiment of the present invention.
Figure 17:
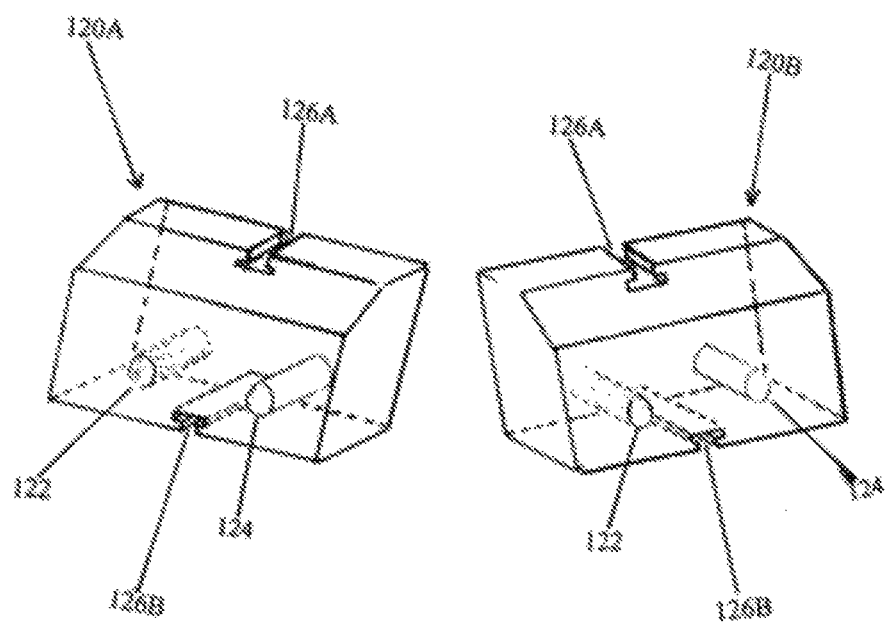
FIG. 17 is a perspective view of the moveable blocks of a device according to an embodiment of the present invention and as depicted in FIGS. 14, 15 and 16.

Referring to FIGS. 13 and 17, the moveable block 120A and 120B comprise four channels: (1) a threaded channel 122 designed to accommodate the screw shaft 136; (2) an unthreaded channel 124 designed to accommodate the screw shaft 136; (3) a channel 126A designed to accept the top railing 116A of the implant; and (4) a channel 126B designed to accept the bottom railing 116B of the implant.

The threaded channel 122 of each moveable block 120A, 120B is designed to accept the shaft 136 of the screw 134 and threadably engage the shaft 136. The unthreaded channel 124 of each moveable block 120A, 120B is designed to accommodate the anatomy of the screw shaft 136, but to maintain a diameter that is slightly larger than the diameter of the screw shaft 136 so as to not engage the screw shaft 136.

The threading of each threaded channel 122 is designed to complement the flighting on the screw 134 that runs through it so as to threadably engage the corresponding moveable block 120A, 120B.

As in the first embodiment, each moveable block 120A, 120B comprises two channels designed to accept guide rails 116A, 116B. In the present embodiment, the guide rail 116A located towards the top 112 center of the implant. Likewise, the guide rail 116B located towards the bottom 146 center of the implant. The guide rails 116A, 116B run along the longitudinal axis (not shown) of the implant. The guide rails 116A, 116B extend from the interior wall of the leading end 104 of the implant to the interior wall of the trailing end 144 of the implant.

FIG. 13 provides an exploded view of the leading end 102 and moveable blocks 120A, 120B of the implant. FIG. 14 depicts the implant in a non-deployed, un-expanded state.

FIG. 15 depicts the implant in a partially deployed, partially expanded state. As will be more fully explained herein, the expandable top 112 of the leading end 102 and the expandable top 112 of the trailing end 128 of the implant are designed to expand upwards. With the expansion of the expandable tops 112, the overall shape of the implant will transition to a more rectangular leading end 102 and trailing end 128 as compared to the implant in a non-deployed, unexpanded state (see FIGS. 9, 10 and 14 for comparison).

FIG. 16 depicts the implant in a deployed and expanded state. As depicted by FIG. 16, the mass of the moveable blocks 120A, 120B of the implant have forced the expandable tops 112 of the implant to expand upwards.

The mode of operation is similar to that of the first embodiment. However, in this embodiment, each screw head 132 is rotated either left or right to force the respective moveable block 120A, 120B to its respective end of the implant.

Referring to moveable block 120A, the screw head 132 is rotated in such a manner that the rotation of the screw shaft 138 forces the flighting 140 of the screw shaft 138 to engage the threaded channel 122 that runs through the moveable block 120A.

The moveable block 120A is thereby forced toward the leading end 102 of the device. The guide rails 116A, 116B of the implant 100 secure the moveable block 120A within the cavity 118 and further ensure that the moveable block 120 follows the desired path.

Referring to moveable block 120B, the screw head 132 is rotated in such a manner that the rotation of the screw shaft 138 forces the flighting 140 of the screw shaft 138 to engage the threaded channel 122 that runs through the moveable block 120B. The moveable block 120B is thereby forced toward the trailing end 128 of the device.

The guide rails 116A, 116B of the implant secure the moveable block 120B within the cavity 118, and further ensure that the moveable block 120 follows the desired path.

As the moveable blocks 120A, 120B travels towards the leading end 102 and trailing end 128 of the implant, the mass of the moveable blocks 120A, 120B forces the expandable tops 108 to expand upwards.

In each moveable block 120A, 120B, the unthreaded channel 124 is designed to provide a pathway for the screw shaft 138 without engaging the shaft. This permits the moveable block 120A, 120B to travel to the desired end of the implant.

In this embodiment, this implant is adjustable on both the leading end 102 and trailing end 128 of the implant. As such, surgeons may adjust the implant as needed to obtain proper tilt, disc height and alignment of the surrounding vertebrae.

Referring to FIGS. 18, 19, 20, 21, 22, 23, 24, 25, 26A, 26B, and 26C, in other embodiments, it is contemplated that the device will comprise an expandable top 108 centered on the latitudinal axis (not shown). In this embodiment, the moveable block 120C is attached to the expandable top 108 so that a single component piece is formed.

Figure 18:
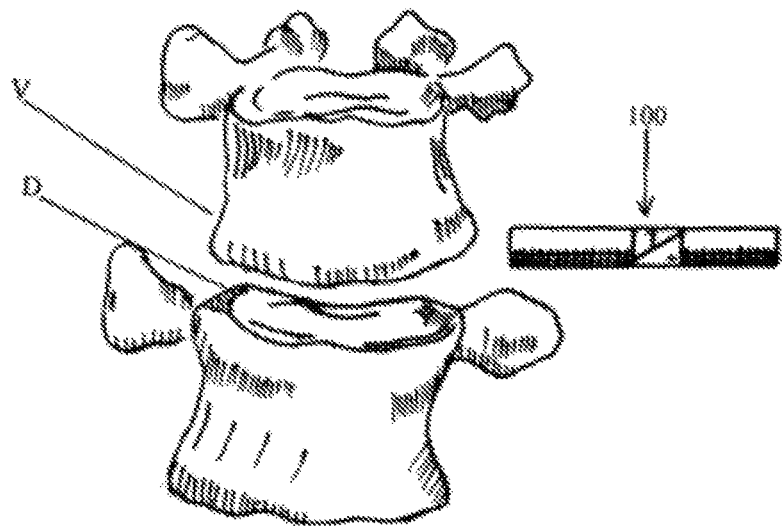
FIG. 18 is a schematic illustration of a device of the present invention prior to insertion in the intervertebral disc space in an unexpanded, non-deployed configuration.
Figure 19:
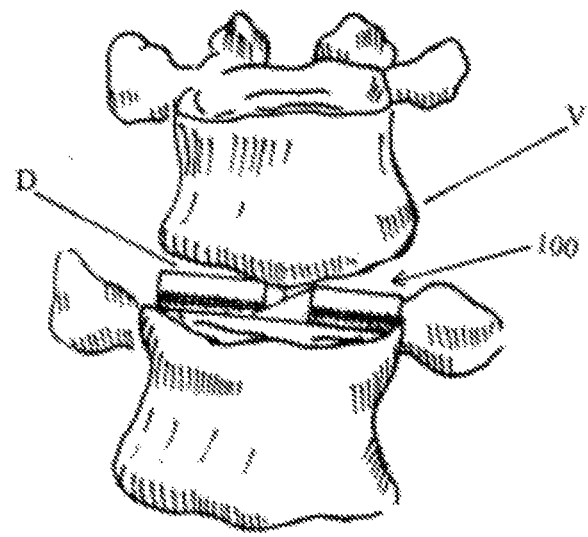
FIG. 19 is a schematic illustration of a device of the present invention positioned in the intervertebral disc space in an unexpanded, non-deployed configuration.
Figure 20:
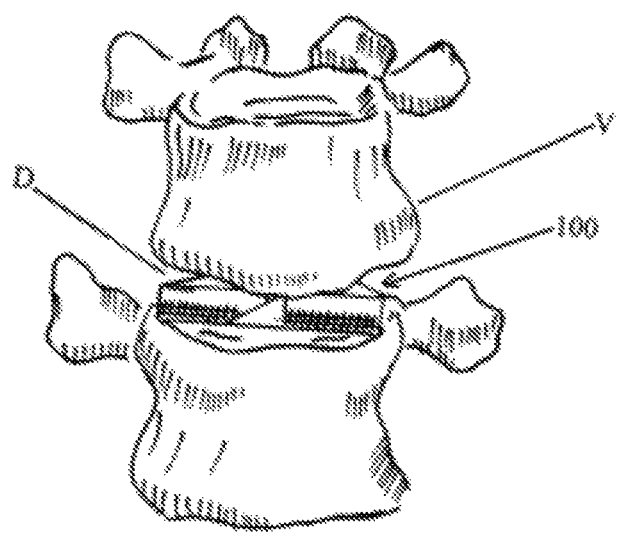
FIG. 20 is a schematic illustration of a device of the present invention positioned in the intervertebral disc space in a partially expanded, partially deployed configuration.
Figure 21:
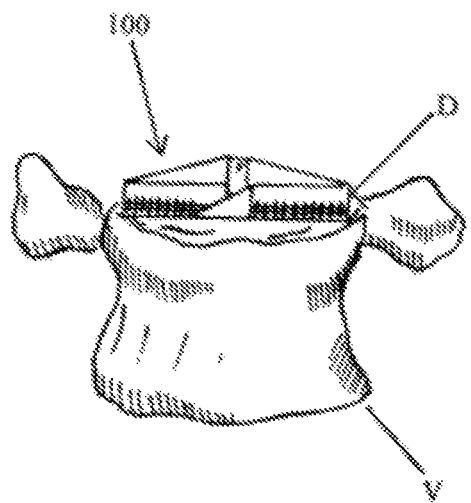
FIG. 21 is a schematic illustration of a device of the present invention positioned in the intervertebral disc space in an expanded, deployed configuration.

FIG. 18 (schematic view in non-deployed, unexpanded state prior to insertion), FIG. 19 (schematic view in non-deployed, unexpanded state after insertion), FIG. 20 (schematic view in partially deployed, partially expanded state), and FIG. 21 (schematic view in deployed, expanded state), generally depicts an intervertebral implant 100. The implant 100 is designed for implantation across a disc space D between two adjacent vertebral bodies V.

Figure 22:
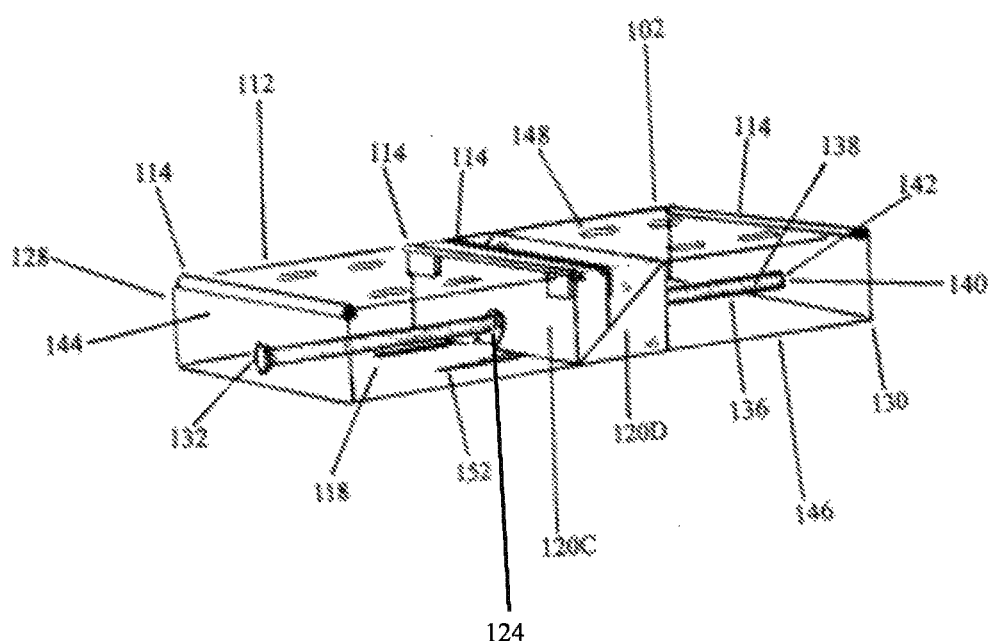
FIG. 22 is a perspective view of a device according to an embodiment of the present invention, in an unexpanded, non-deployed configuration.
Figure 23:
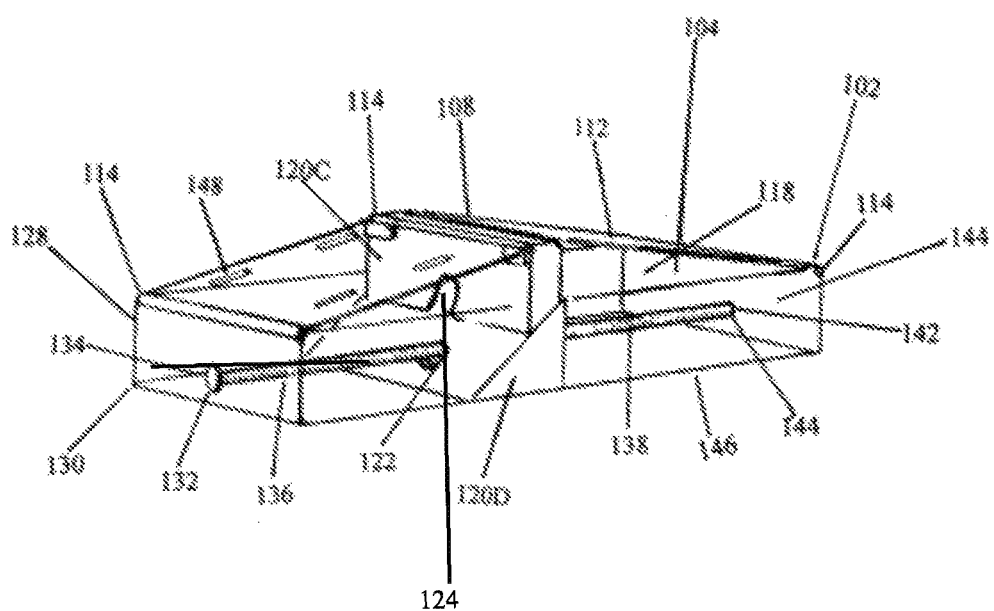
FIG. 23 is a perspective view of a device according to an embodiment of the present invention, in an expanded, deployed configuration.
Figure 24:
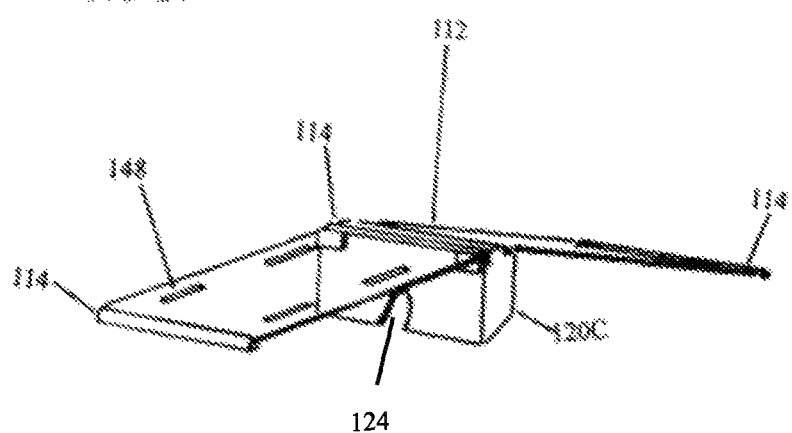
FIG. 24 is a perspective view of the expandable tops connected to the moveable block of a device according to an embodiment of the present invention, in an unexpanded, non-deployed configuration.
Figure 25:
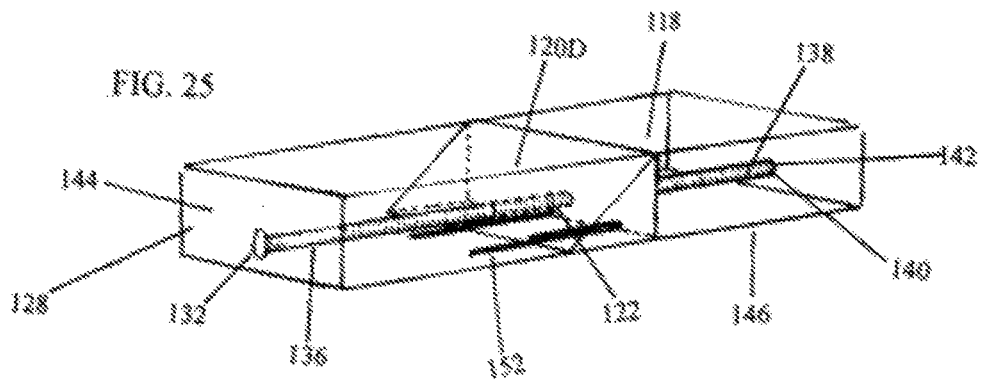
FIG. 25 is a perspective view of the body of a device according to an embodiment of the present invention, in an unexpanded, non-deployed configuration. The expandable tops connected to the moveable block is removed for illustration purposes.
Figure 26A:
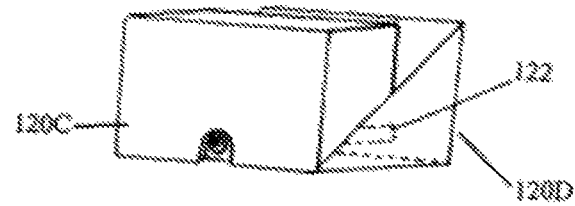
FIG. 26A is a perspective view of the moveable blocks of a device according to an embodiment of the present invention, in an unexpanded, non-deployed configuration. The screw is removed for illustration purposes.
Figure 26B:
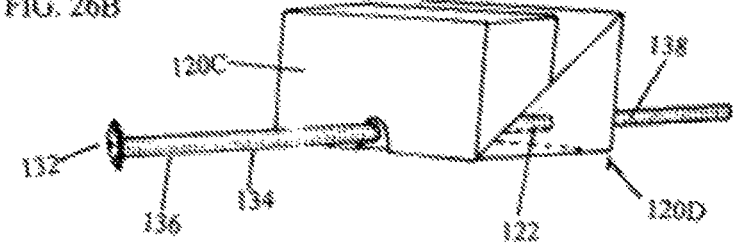
FIG. 26B is a perspective view of the moveable blocks of a device according to an embodiment of the present invention, in an unexpanded, non-deployed configuration.
Figure 26C:
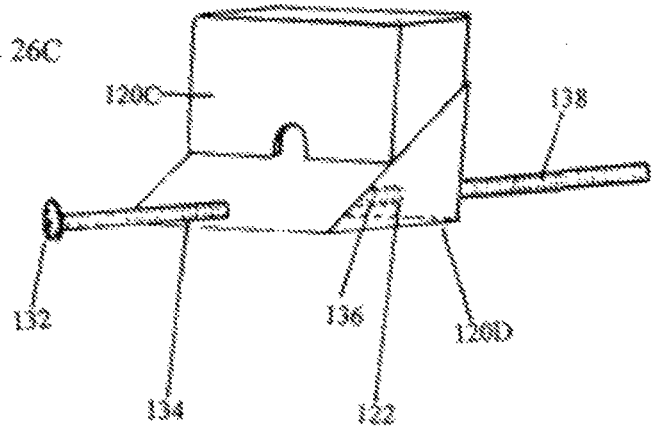
FIG. 26C is a perspective view of the moveable blocks of a device according to an embodiment of the present invention, in an expanded, deployed configuration.

Referring to FIGS. 22 (implant in an unexpanded, non-deployed state) and 23 (implant in expanded and deployed state), in this embodiment, the implant comprises a leading end 102 with an expandable top 108. The expandable top 108 is secured to the body of moveable block 120C with two hinges 114. Each hinge 114 extends the length of moveable block 120C, along the left and right sides of the top of the moveable block 120C.

However, in an alternate embodiment, it is contemplated that the two halves of the expandable top will connect to each other by way of a hinge. In the alternative, the two halves of the expandable top may connect to a rectangular strip by way of hinges.

The expandable top 108 of the implant is also connect to the body of the implant at the leading end 102 and trailing end 128 of the implant. The expandable top 108 is connected by a hinge 114 at the leading end 102 of the implant and a hinge 114 trailing end 128 of the implant. As such, in this embodiment, the implant is capable of upward expansion in the center of the device. (See also FIG. 24).

The screw head 132 is located at the trailing end 128 of the implant. The screw head 132 can be configured to accept the distal end of a driving tool (not shown). The driving tool may be used to assist with the placement of the implant into the intervertebral disc space and, or to rotationally turn screw head 132.

The implant comprises a hollow interior 118 that is in constant communication with the interior walls of the implant. The hollow interior comprises: (1) two moveable blocks 120C, 120D that are secured by; (2) the screw shafts 136; and (3) a guide rail 116B with a stopper 152 to secure and guide moveable block 120D.

Referring to FIGS. 24, 25, 26A, 26B and 26C, moveable blocks 120C, 120D are slideably coupled with one another. Overall, moveable block 120C comprises the shape of a rectangular prism. However, the bottom half of the moveable block 120C is angled so that it sits flush with moveable block 120D. The angle formed by the bottom half of moveable block 120C complements the angle formed by moveable block 120D. Moveable block 120C is sized to fit within the cavity 118 of the implant. In most embodiments, moveable block 120C will generally range from about 0.25 to 15 millimeters (mm) in width. The device will generally range from 0.5 to 25 millimeters (mm) in length.

Moveable block 120C further comprises an unthreaded channel 124 designed to accommodate the screw shaft 136. In this embodiment, the unthreaded channel 124 generally forms the shape of a semi-circle. However, in other embodiments, the unthreaded channel 124 may be of any shape that will accommodate the screw shaft 136.

Moveable block 120D comprises the shape of a triangular prism. The base of the prism is formed by two congruent triangles that are flush with the interior walls of the implant. The faces of the prism are rectangular in shape. The angles of the congruent triangles of the prism complement moveable block 120C such that moveable block 120C and moveable block 120D sit flush with one another.

Moveable block 120D comprises a threaded channel 122 designed to accommodate and engage the screw shaft 136.

Moveable block 120D is sized to fit within the cavity 118 of the implant. In most embodiments, moveable block 120D will generally range from about 0.5 to 30 millimeters (mm) in width. The device will generally range from 0.5 to 25 millimeters (mm) in length.

Referring to FIGS. 18, 19, 20 and 21, the mode of operation is similar to that of the first embodiment. The above parts work in tandem to facilitate the expansion of the implant. In its non-deployed position, the moveable blocks 120C, 120D are centered on the latitudinal axis (not shown) of the implant. (See also FIGS. 22 and 23).

Referring the FIGS. 22, 23, 26A, 26B and 26C, the implant is deployed by the rotation of the screw head 132. The screw head 132 is rotated in such a manner that the rotation of the screw shaft 136 forces the flighting 138 of the screw shaft 136 to engage the threaded channel 122 that runs through the moveable block 120D.

As the implant is deployed, moveable block 120D travels along the guide rail 116B from the center of the implant to the trailing end 128 of the implant. The moveable block 120D stops when it reaches a stopper 152. (see FIG. 25).

The movement of moveable block 120D forces moveable block 120C to travel up the body of moveable block 120D. As moveable block 120C travels up the body of moveable block 120D, the mass of the moveable block 120C forces the expandable top 108 to expand upwards.

In this embodiment, this implant is adjustable at the center of the implant. As such, surgeons may adjust the implant as needed to obtain proper tilt, disc height and alignment of the surrounding vertebrae.

Figure 28:
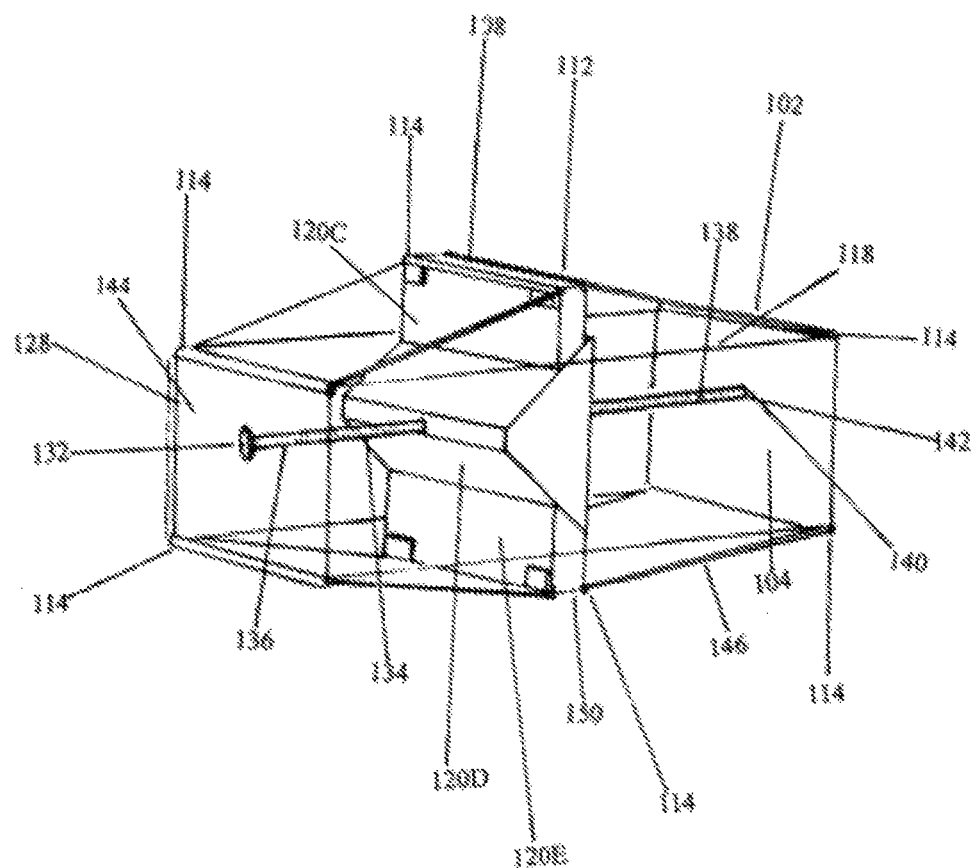
FIG. 28 is a perspective view of a device according to an embodiment of the present invention, in an expanded, deployed configuration.

Referring to FIGS. 27 and 28, in other embodiments, it is contemplated that the device will comprise an expandable top 108 centered on the latitudinal axis (not shown) and an expandable bottom 150 centered on the latitudinal axis (not shown) of the implant.

Referring to FIG. 27 (implant in an unexpanded, non-deployed state) and 28 (implant in expanded and deployed state), in this embodiment, the implant comprises a leading end 102 with an expandable top 108 and expandable bottom 150.

As in the embodiment depicted by FIGS. 18, 19, 20, 21, 22, 23, 24, 25, 26A, 26B, and 26C, the expandable top 108 is secured to the body of moveable block 120C with two hinges 114. Each hinge 114 extends the length of moveable block 120C, along the left and right sides of the top of the moveable block 120C. Similarly, the expandable bottom 150 is secured to the body of moveable block 120E with two hinges 114. Each hinge 114 extends the length of moveable block 120E, along the left and right sides of the top of the moveable block 120E.

The expandable top 108 is secured to the body of the implant with a hinge 114 that is located at the leading end 102 of the implant and a hinge located at the trailing end 128 of the implant. The expandable bottom 150 is secured to the body of the implant with a hinge 114 that is located at the leading end 102 of the implant and a hinge 114 located at the trailing end 128 of the implant.

In an alternate embodiment, it is contemplated that the two halves of the expandable top may connect at a central hinge or to a rectangular strip centered on the latitudinal axis of the implant by way of hinges. The expandable bottom of the implant may be connected to the body of the implant in a similar manner.

In this embodiment, the implant is capable of upward expansion and downward expansion at the center of the implant.

The screw head 132 is located at the trailing end 128 of the implant. The screw head 132 can be configured to accept the distal end of a driving tool (not shown). The driving tool may be used to assist with the placement of the implant into the intervertebral disc space and, or to rotationally turn screw head 132.

The implant comprises a cavity 118 that is in constant communication with the interior walls of the implant. The hollow interior comprises: (1) three moveable blocks 120C, 120D, 120E; (2) the screw shaft 136; and (3) a guide rail 116B with a stopper 152 used to secure and guide moveable block 120D.

The moveable blocks 120C, 120D, 120E are slideably coupled with one another. Overall, moveable block 120C and moveable block 120E comprise the shape of a rectangular prism. However, the bottom half of the moveable block 120C and top of moveable block 120E are angled so that they sit flush with moveable block 120D (forming a wedge-like tip). The angle formed by the bottom half of moveable block 120C and the angle formed by the top half of moveable block 120E complement the angle formed by moveable block 120D. Moveable block 120C and moveable block 120E are sized to fit within the cavity 118 of the implant. In most embodiments, moveable block 120C and moveable block 120E will generally range from about 0.25 to 15 millimeters (mm) in width. The device will generally range from 0.5 to 25 millimeters (mm) in length.

Moveable block 120C and moveable block 120E further comprise an unthreaded channel 124 designed to accommodate the screw shaft 136.

Moveable block 120D comprises the shape of a triangular prism. The base of the prism is formed by two congruent triangles that are flush with the interior walls of the implant. The faces of the prism are rectangular in shape. The angles of the congruent triangles of the prism complement moveable block 120C and moveable block 120E such that moveable block 120C and moveable block 120E sit flush with moveable block 120D.

Moveable block 120D comprises a threaded channel 122 designed to accommodate and engage the screw shaft 136.

Moveable block 120D is sized to fit within the cavity 118 of the implant. In most embodiments, moveable block 120D will generally range from about 0.5 to 30 millimeters (mm) in width. The device will generally range from 0.5 to 25 millimeters (mm) in length.

The mode of operation is similar to that of the first embodiment. The above parts work in tandem to facilitate the expansion of the implant. In its non-deployed position, the moveable blocks 120C, 120D, 120E are centered on the latitudinal axis (not shown) of the implant.

The implant is deployed by the rotation of the screw head 132. The screw head 132 is rotated in such a manner that the rotation of the screw shaft 136 forces the flighting 138 of the screw shaft 136 to engage the threaded channel 122 that runs through the moveable block 120D. As the implant is deployed, moveable block 120D travels along the rail system 116B from the center of the implant to the trailing end 128 of the implant. The moveable block 120D stops when it reaches a stopper 152.

The movement of moveable block 120D forces moveable block 120C to travel up the body of moveable block 120D. As moveable block 120C travels up the body of moveable block 120D, the mass of the moveable block 120C forces the expandable top 108 to expand upwards.

Simultaneously, the movement of moveable block 120D forces moveable block 120E to travel down the body of moveable block 120D. As moveable block 120E travels down the body of moveable block 120D, the mass of the moveable block 120E forces the expandable bottom 150 to expand downwards.

In this embodiment, this implant is adjustable at the center of the implant. As such, surgeons may adjust the implant as needed to obtain proper tilt, disc height and alignment of the surrounding vertebrae.

The foregoing description and examples have been set forth merely to illustrate the invention and are not intended as being limiting. Each of the disclosed aspects and embodiments of the present invention may be considered individually or in combination with other aspects, embodiments and variations of the invention. Further, while certain features of embodiments of the present invention may be shown in only certain figures, such features can be incorporated into other embodiments shown in other figures while remaining within the scope of the present invention.

In addition, unless otherwise specified, none of the steps of the methods of the present invention are confined to any particular order of performance. Modifications of the disclosed embodiments incorporating the spirit and substance of the invention may occur to persons skilled in the art and such modifications are within the scope of the present invention. Furthermore, all references cited herein are incorporated by reference in their entirety.

What is claimed is:

1. An expandable intervertebral spacer for stabilizing vertebral bodies comprising:
   a body having a leading end, a trailing end, a top wall, a bottom wall, and first and second side walls extending between said top wall and said bottom wall, wherein said bottom wall and said top wall generally define a hollow interior of the body and contain a plurality of openings, and said interior of the body includes a rail extending from said leading end to said trailing end,
   a moveable block, configured to provide support for said intervertebral spacer and dimensioned to slide within said generally hollow interior of the body, and having a leading end, a trailing end, a top surface, a bottom surface and first and second side surfaces, and including at least one threaded aperture and at least one channel,
   a screw dimensioned to be received within the threaded aperture of said moveable block and extending from the leading end to the trailing end of the body, such that rotation of the screw causes said moveable block to translate along the interior of the body from the trailing end of the body to the leading end of the body,
   wherein at least one of said top wall and said bottom wall of the body further includes a hinge such that at least a portion of at least one of said top wall and said bottom wall is capable of pivoting about said hinge, and
   wherein the height of said top wall and, or said bottom wall has a second height that is greater than the first height when said moveable block is positioned at said trailing end or said leading end of the implant,
   wherein said leading end and, or said trailing end transitions from an angular shape in its unexpanded state to a substantially rectangular shape in its partially expanded and, or expanded state,
   wherein said the expansion of said leading end and, or said trailing end provides for the dynamic stabilization of adjacent vertebral bodies,
   wherein the intervertebral spacer in a partially expanded or expanded state provides structural support, adjustment and stabilization of intervertebral bodies that said top wall and said bottom wall contact, and
   a locking element for maintaining the moveable body in the expanded state.

2. The expandable intervertebral spacer of claim 1, wherein said moveable block slides from the proximal end to the distal end of the implant.

3. The expandable intervertebral spacer of claim 1, wherein said locking element is a locking screw.

4. The expandable intervertebral spacer of claim 1, wherein said locking screw has a length sufficient to extend from the proximal end of the implant to the distal end of the implant.

5. The expandable intervertebral spacer of claim 1, wherein said expandable intervertebral spacer is generally rectangular.

6. The expandable intervertebral spacer of claim 1, wherein the leading end of the expandable intervertebral spacer is one of wedge shaped, rounded, beveled, rectangular or polygonal.

7. A method for stabilizing adjacent vertebral bodies, comprising:
   accessing an intervertebral disc space,
   inserting an expandable intervertebral spacer into the intervertebral disc space,
   a body having a leading end, a trailing end, a top wall, a bottom wall, and first and second side walls extending between said top wall and said bottom wall, wherein said bottom wall and said top wall generally define a hollow interior of the body and contain a plurality of openings, and said interior of the body includes a rail extending from said leading end to said trailing end, and a moveable block that is dimensioned to slide within said generally hollow interior of the body, and having a leading end, a trailing end, a top surface, a bottom surface and first and second side surfaces, and including at least one threaded aperture and at least one channel, a screw dimensioned to be received within the threaded aperture of said moveable block, and extending from the leading end to the trailing end of the body, such that rotation of the screw causes said moveable block to translate along the interior of the body from the trailing end of the body to the leading end of the body, wherein at least one of said top wall and said bottom wall of the body further includes a hinge such that at least a portion of at least one of said top wall and said bottom wall is capable of pivoting about said hinge, and wherein the height of said top wall and said bottom wall has a second height that is greater than the first height when said moveable block is positioned at said trailing end or said leading end of the implant,
   engaging the screw head of the implant by using a driving tool to rotationally turn screw head,
   wherein the rotation of the screw shaft forces the fighting of the screw to engage the threaded channel that runs through said moveable block,
   wherein said moveable block is forced toward the leading end or the trailing end of the implant,
   wherein the mass of said moveable block causes said top wall or said bottom wall to expand,
   wherein the expansion of said implant provides for dynamic stabilization of adjacent vertebral bodies,
   locking said moveable block in the deployed state with a locking element.

8. The method of claim 7, further comprising the step of inserting bone growth material on or into the expandable intervertebral spacer.

9. The method of claim 7 wherein the disc space is accessed from a posterior, anterior or lateral approach.

* * * * *